United States Patent
Enomoto

(10) Patent No.: US 7,440,005 B2
(45) Date of Patent: Oct. 21, 2008

(54) ENDOSCOPE

(75) Inventor: Takayuki Enomoto, Saitama (JP)

(73) Assignee: Hoya Corporation, Tokyo (JP)

( * ) Notice: Subject to any disclaimer, the term of this patent is extended or adjusted under 35 U.S.C. 154(b) by 135 days.

(21) Appl. No.: 11/620,198

(22) Filed: Jan. 5, 2007

(65) Prior Publication Data

US 2007/0167673 A1  Jul. 19, 2007

(30) Foreign Application Priority Data

Jan. 13, 2006  (JP) .............................. 2006-005974

(51) Int. Cl.
*H04N 7/18* (2006.01)

(52) U.S. Cl. .............................. 348/72; 348/65; 348/75; 348/73; 348/76; 348/77; 600/118; 600/113; 600/109; 600/107

(58) Field of Classification Search .................... 348/72, 348/65, 75, 73, 76, 77; 600/118, 113, 109, 600/117

See application file for complete search history.

(56) References Cited

U.S. PATENT DOCUMENTS 6,473,116 B1 * 10/2002 Takahashi .................... 348/65
6,635,011 B1    10/2003 Ozawa et al.
2003/0160865 A1 *  8/2003 Takahashi .................... 348/65
2006/0038882 A1 *  2/2006 Enomoto ...................... 348/65
2006/0178565 A1    8/2006 Matsui et al.

* cited by examiner

*Primary Examiner*—Shawn An
(74) *Attorney, Agent, or Firm*—Greenblum & Bernstein, P.L.C.

(57) ABSTRACT

In an endoscope, scopes that include a scope-side memory and a connector are selectively and detachably connected to a processor that includes a processor-side memory and a connection member. A parameter stored in the scope-side memory can be written to the processor-side memory. The connector that is connectable to the connection member is used for connecting the scope to the processor. When the connection member that is movable is in the first position, the connector is detachably connectable to the connection member. When the connection member is in the second position, the subject is observable. When the connection member is moved from the first position to the second position, the parameter is written to the processor-side memory. When the connection member is moved from the second position to the first position, the parameter is written to the scope-side memory.

12 Claims, 5 Drawing Sheets

FIG. 5

| ROTATIONAL POSITIONS | SECONDARY CIRCUIT | BUFFER CIRCUIT | CONNECTION OF SCOPE |
|---|---|---|---|
| Pos3 | OFF | OFF | NO |
| Pos1 | ON | OFF | CONNECTABLE |
| Pos4 | ON | OFF ↔ ON | YES |
| Pos5 | ON | ON | YES(PARAMETERS WRITTEN) |
| Pos2 | ON | ON | YES |

ENDOSCOPE

BACKGROUND OF THE INVENTION

1. Field of the Invention

The present invention relates to an endoscope, especially to an endoscope that enables a suitable observation of a subject according to a scope in use.

2. Description of the Related Art

An electronic endoscope generally includes a scope that has a light guide to lead light to a subject, an electronic camera, and other components, and a processor that processes image data based on image signals generated in and transmitted from the scope. To the processor, one of a plurality of scopes which is selected in accordance with a purpose of an observation of a subject is connected detachably, and then the scope is used. Thus, a connection device for connecting a scope to a processor has been known.

In a general electronic endoscope, when a scope is connected to a processor, some of various parameters that were stored in the scope and that are suitable for observing or photographing a subject by the scope are transmitted to the processor for usage.

When a scope of an electronic endoscope connected to a processor is exchanged, parameters that have been stored in the exchanged scope to be used for observing a subject, may be overwritten by other parameters that have been stored in a scope that is newly connected to the processor. In such a case, suitable parameters may not be used because a scope in which original parameters are deleted by overwriting is used, so that some trouble may occur in a subject observation.

SUMMARY OF THE INVENTION

Therefore, an objective of the present invention is to provide an endoscope where parameters suitable for a subject observation in accordance with a scope in usage are used reliably.

In an endoscope according to the present invention, a plurality of scopes are selectively and detachably connected to a processor. The endoscope includes a scope-side memory, a connector, a processor-side memory, and a connection member. The scope-side memory is provided in each of the scopes, and a parameter used for observing a subject is stored in the scope-side memory. The connector is provided in each of the scopes, and the connector is used for connecting the scope to the processor. The processor-side memory is provided in the processor. The connection member is provided in the processor, and the connector is connected to the connection member. The connection member is movable between a first position and a second position. The connector is detachably connectable to the connection member when the connection member is in the first position. The subject is observable when the connection member is in the second position. The parameter is written in the processor-side memory when the connection member is moved from the first position to the second position. The parameter is written in the scope-side memory when the connection member is moved from the second position to the first position.

The connection member may include a rotatable lever. The connection member may be movable further to a third position that is not between the first position and the second position, and the processor and the scope may not operate when the connection member is in the third position.

The processor may further include a first electric circuit that can be connected to the scope electrically. The first electric circuit may not operate when the connection member is in the first position, and the first electric circuit may operate when the connection member is in the second position.

The connection member may be movable further to a fourth position where the on and off state of the first electric circuit is switched, and to a fifth position where the parameter is written in the scope-side memory or in the processor-side memory. The fourth position and the fifth position may be between the first position and the second position.

The fifth position may be between the second position and the fourth position.

The processor may further include a second electric circuit in which the processor-side memory is provided, and the second electric circuit may operate when the connection member is in the first position or in the second position.

The second electric circuit may include an image processor that processes an image of the subject, and the parameter may be used for processing the image of the subject.

To a processor according to the present invention, one of a plurality of scopes is selectively and detachably connected. Each of the scopes includes a scope-side memory in which a parameter used for observing a subject is stored, and a connector that is used for connecting the scope to the processor. The processor includes a processor-side memory and a connection member. To the connection member, the connector is connected. The connection member is movable between a first position and a second position. The connector is detachably connectable to the connection member when the connection member is in the first position. The subject is observable when the connection member is in the second position. The parameter is written in the processor-side memory when the connection member is moved from the first position to the second position. The parameter is written in the scope-side memory when the connection member is moved from the second position to the first position.

A scope connection mechanism according to the present invention is provided in a processor to which one of a plurality of scopes is selectively and detachably connected. Each of the scopes includes a scope-side memory in which a parameter used for observing a subject is stored and a connector that is used for connecting the scope to the processor. The processor includes a processor-side memory. The scope connection mechanism includes a connection member to which the connector is connected. The connection member is movable between a first position and a second position. The connector is detachably connectable to the connection member when the connection member is in the first position. The subject is observable when the connection member is in the second position. The parameter is written in the processor-side memory when the connection member is moved from the first position to the second position. The parameter is written in the scope-side memory when the connection member is moved from the second position to the first position.

A scope according to the present invention is selectively and detachably connected to a processor including a processor-side memory. The scope includes a scope-side memory. In the scope-side memory, a parameter used for observing a subject is stored. The parameter is written to the processor-side memory and the subject is observable when the scope is connected to the processor. The parameter is written to the scope-side memory when scope is detached from the processor, so that the parameter written to the processor-side memory lastly is stored in the scope-side memory.

The parameter may be used for processing an image of the subject.

BRIEF DESCRIPTION OF THE DRAWINGS

The present invention will be better understood from the description of the preferred embodiment of the invention set forth below, together with the accompanying drawings, in which:

FIG. 5 is a view representing power source conditions of circuits in a processor and connection conditions of a scope that correspond to the rotational positions of the lever.

DESCRIPTION OF THE PREFERRED EMBODIMENT

Hereinafter, the preferred embodiment of the present invention is described with reference to the attached drawings.

Figure 1:
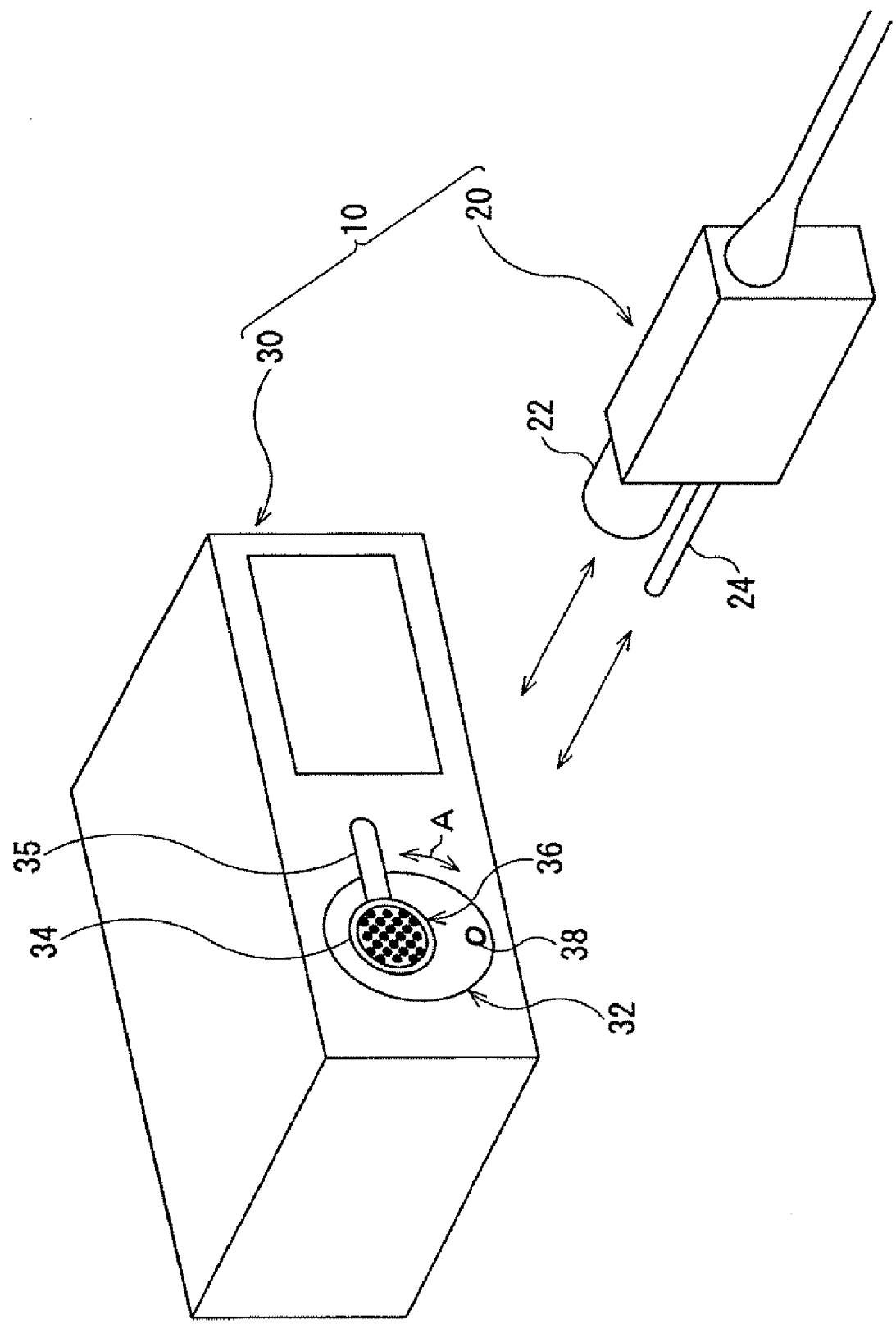
FIG. 1 is a perspective view representing an electronic endoscope of the embodiment approximately.

An electronic endoscope 10 includes a scope 20 and a processor 30, as represented in FIG. 1. The scope 20 is used for photographing and observing a subject, which is inside a body cavity. The processor 30 processes image signals transferred from the scope 20. To the processor 30, a plurality of scopes, including the scope 20, can be connected. One of the scopes that is selected in accordance with the purpose of an observation of a subject is detachably connected to the processor 30, and then is used.

In the scope 20, a signal connector 22 and a light guide connector 24 are provided. In the processor 30, a scope connection mechanism 32 is provided. In the scope connection mechanism 32, a rotation lever 36, which includes a signal connector insertion mouth 34, and a light guide connector insertion mouth 38 are provided.

The signal connector 22 and the light guide connector 24 are inserted into the signal connector insertion mouth 34 and the light guide connector insertion mouth 38, respectively, so that the scope 20 is connected to the processor 30. Note that the rotation lever 36 rotates by operations of a user holding a handle 35, as the arrow A represents, and then the scope 20 can be connected to or detached from the processor 30 when the rotation lever 36 is in a predetermined rotational position.

Figure 2:
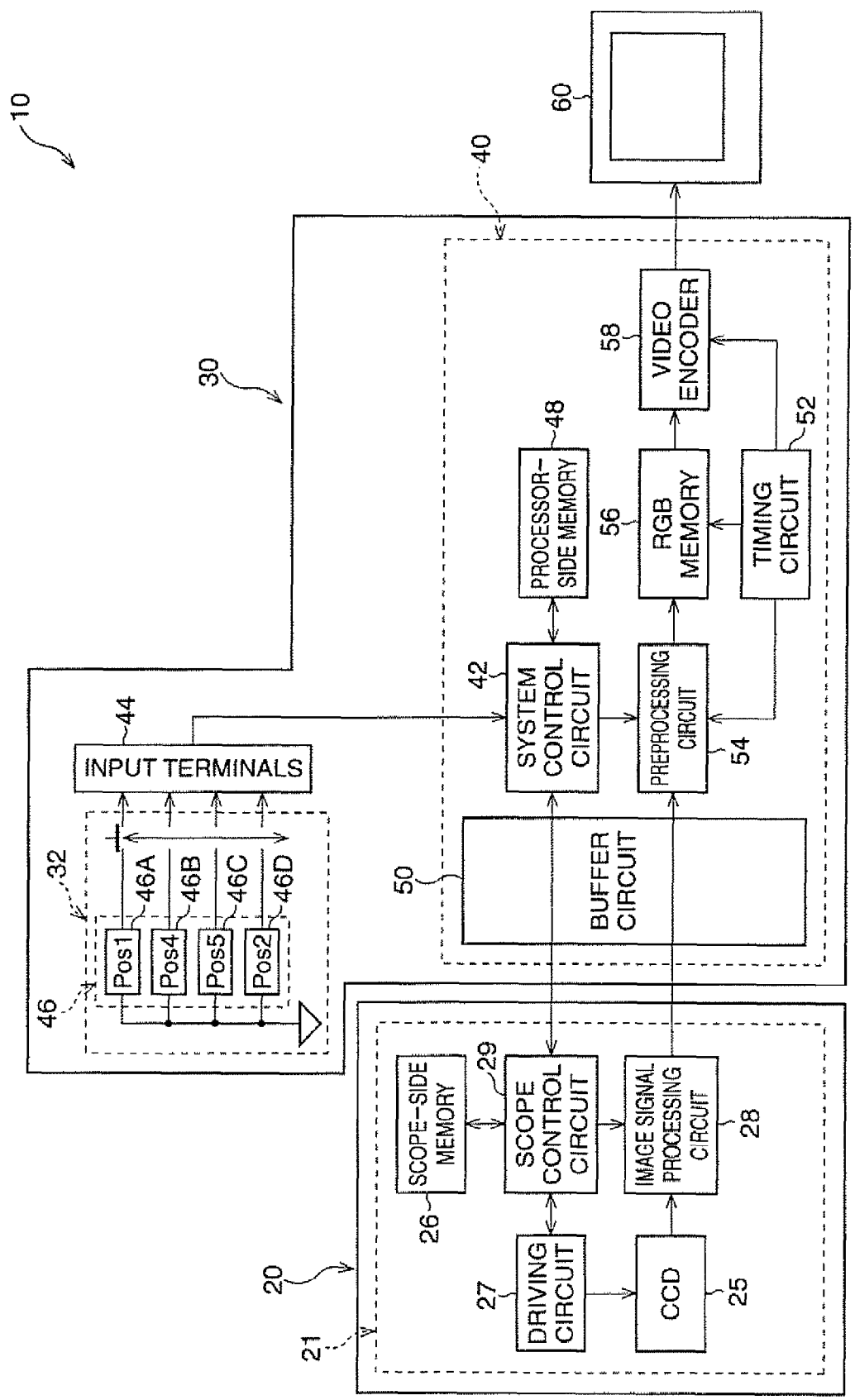
FIG. 2 is a block diagram of the electronic endoscope.

As represented in FIG. 2, in the processor 30, a primary circuit in which a light source and a power source are provided (all not shown) and a secondary circuit (the second electric circuit) 40 are provided. The second electric circuit includes a system control circuit 42 for controlling the entirety of the processor 30. In the scope connection mechanism 32, a position switch 46 that includes first to fourth positional switches 46A to 46D is provided. When the rotation lever 36 is rotated, corresponding to the change of the rotational position (explained below) of the rotation lever 36, the on and off states of the first to fourth positional switches 46A to 46D are varied. As a result, signals representing the rotational positions of the rotation lever 36 are transmitted to the system control circuit 42 via input terminal 44, in accordance with the movement of the rotation lever 36.

In the scope 20, a scope circuit 21 is provided. The scope circuit 21 includes a CCD 25, a scope-side memory 26 in which parameters used for observing and photographing a subject are stored, a driving circuit 27 that drives the CCD 25, an image signal processing circuit 28 that processes image data transmitted from the CCD 25, and a scope control circuit 29 that controls these elements.

The parameters stored in the scope-side memory 26 are read under the control of the system control circuit 42 that has received predetermined signals, such as switch signals, from the third positional switch 46C via the scope control circuit 29. The read parameters are temporarily written in a processor-side memory 48, and then are used for observing a subject. As a communication system between the scope control circuit 29 and the system control circuit 42, for example, two-line serial communication is adopted.

In the parameters, various data used for observing a subject suitably are included. For example, white balance data, gamma correction data, color information for adjusting the subject image, and data representing the type of the CCD 25 provided in the scope 20 are included in the parameters.

Next, generation of a subject image is explained. Illuminating light emitted by the light source, and transmitted in a light guide (not shown), is emitted to a subject of a body cavity from the end of the scope 20. Illuminated light reflected off the subject enters the light receiving surface (not shown) of the CCD 25 provided at the end of the scope 20. Then, image signals representing the subject are generated by the CCD 25 driven by the driving circuit 27.

The luminance signal Y and the color-difference signals Cb and Cr are generated by processing the image signals. The luminance signal Y and the color-difference signals Cb and Cr are transferred to the image signal processing circuit 28, and predetermined processes, such as contour emphasis, white balance adjustment, and gain adjustment, are carried out. At the time, parameters read from the scope-side memory 26 and written in the processor-side memory 48 are used.

For example, processes explained below are carried out based on the read parameters, such that, if the scope 20 is for an observation with fluorescent light, signal level is made higher because the level of the image signal generated by fluorescent light is lower than that generated by reflected light of white light, and if a cut filter for cutting off a predetermined component of light, such as blue light, is used, gain of blue is made higher.

Image signals to which predetermined processes are carried out are transmitted to a preprocessing circuit 54 under the control of a timing circuit 52, then are digitized. On the digitized image signals, various processes, such as white balance adjustment and gamma correction are carried out, then the image signals are stored in an RGB memory 56. At the time, the parameters stored in the processor-side memory 48 are also used in the white balance adjustment and the gamma correction.

Digitized image signals are transmitted to a video encoder 58 via the RGB memory 56. In the video encoder 58, video signals are generated based on the image signals, and the video signals are transmitted to a monitor 60. As a result, a subject image is displayed on the monitor 60.

In the secondary circuit 40, a buffer circuit 50 (the first electric circuit) that is electrically connectable to the scope circuit 21 is provided. The buffer circuit 50 is connected to the secondary circuit 40 via an insulation type DC/DC converter and a photo-coupler (both not shown), so that negative effects on the scope circuit 21 and the secondary circuit 40, or breakage thereof, due to short-circuiting and so on, are prevented. Safety for a user from an electric shock is also ensured.

When the scope 20 is detached from the processor 30, for example, when an observation of a subject has ended, or when the scope 20 is exchanged with another scope, it is required that the rotation lever 36 be moved to a predetermined position. At the time, parameters temporarily stored in the processor-side memory 48 are read under the control of the system control circuit 42 that has received signals representing the movement of the rotation lever 36 (such as the signals from the third positional switch 46C). Then, the parameters are written in the scope-side memory 26 via the scope control circuit 29.

As a result, the parameters previously stored in the scope-side memory 26 are reliably memorized; after that, when a scope other than the scope 20 is connected to the processor 30 and the electronic endoscope 10 is used, the values of the parameters of the scope 20 are replaced by those of the newly connected scope in the processor-side memory 48 and are used.

Figure 3:
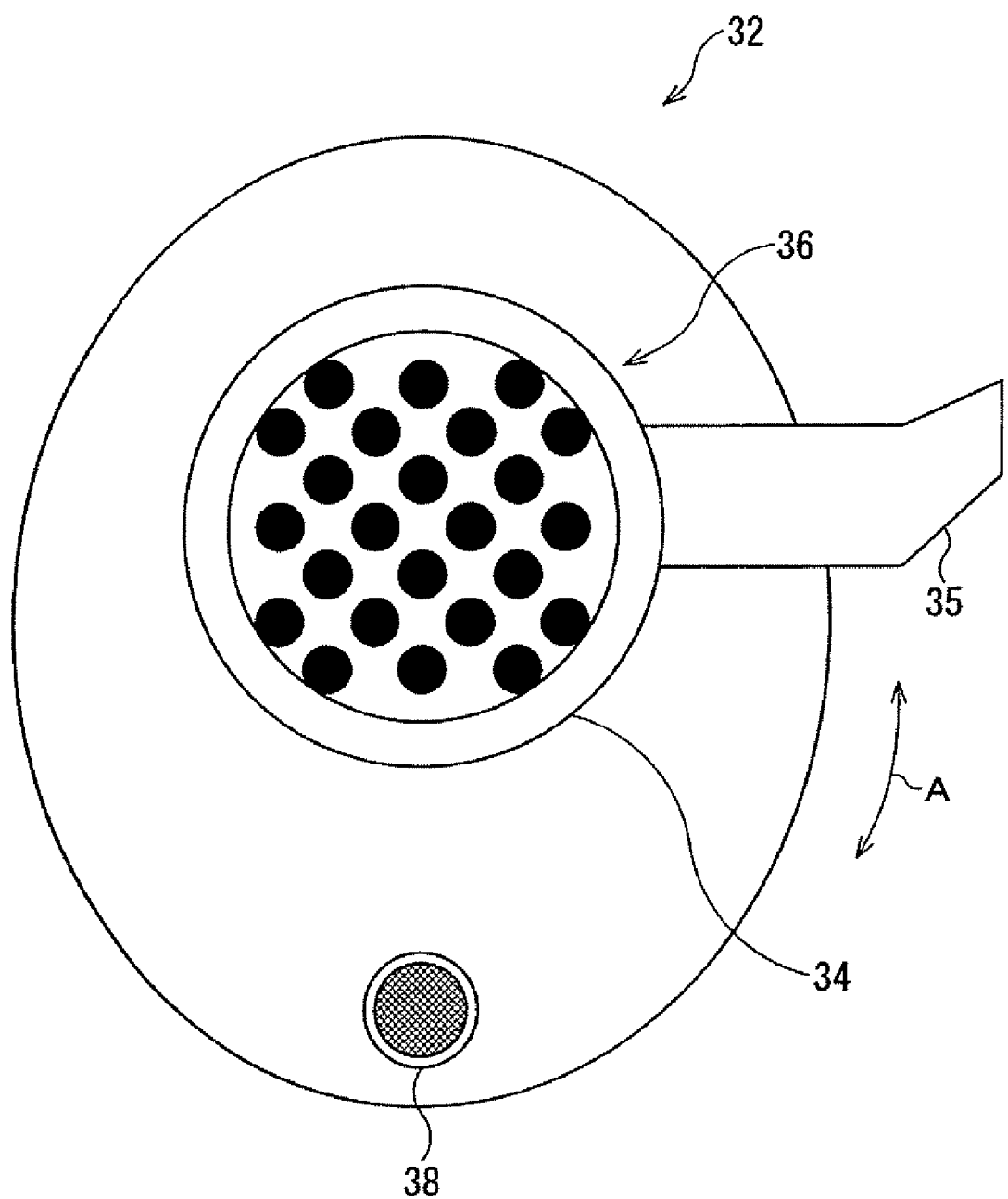
FIG. 3 is a front view representing a scope connection mechanism where a connector of the scope is detached.

When the rotation lever 36 is in a rotational position where the handle 35 is horizontal (hereinafter called the "first position"), as represented in FIG. 3, the signal connector 22 (see FIG. 1) and the light guide connector 24 (also see FIG. 1) are connectable to and detachable from the scope connection mechanism 32. That is, when the rotation lever 36 is in the first position, the scope 20 is connectable to and detachable from the processor 30.

Figure 4A:
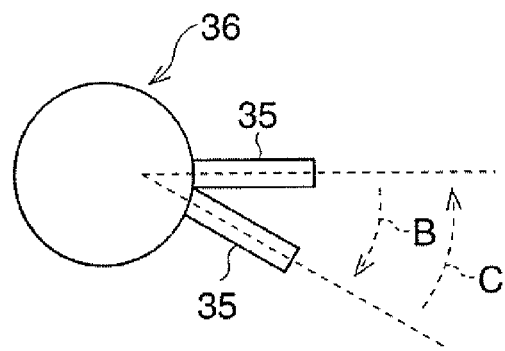
FIG. 4 is a view representing rotational positions of a lever approximately.

When the handle 35 is moved downward from the first position, as the arrow B represents (see FIG. 4(A)), the signal connector 22 and the light guide connector 24 are held by the scope connection mechanism 32, in an inserted state.

Figure 4B:
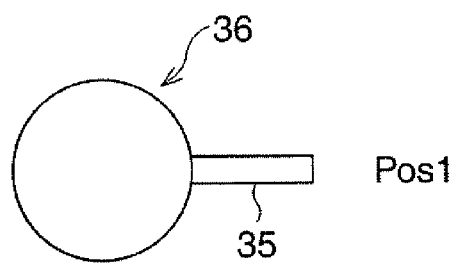
Figure 4C:
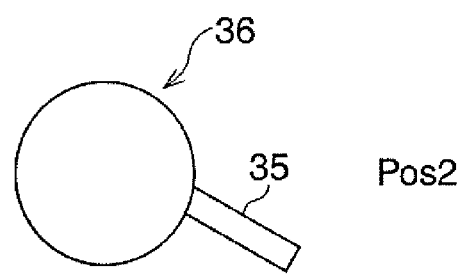

When the rotation lever 36 is in a position where the handle 35 is in the lowest position among its movable positions (hereinafter called the "second position") a subject can be observed by the electronic endoscope 10. Note that the first position is represented by "Pos 1", and the second position is represented by "Pos 2" in FIG. 4(B), 4(C), and in FIG. 5.

When the rotation lever 36 is moved from the second position to the first position as the arrow C represents, in the situation where the scope 20 has been connected to the processor 30, the signal connector 22, and the light guide connector 24 are unlocked. Then, when the rotation lever 36 reaches the first position, a subject can not be observed as explained below, and the scope 20 becomes detachable from the processor 30.

Figure 4D:
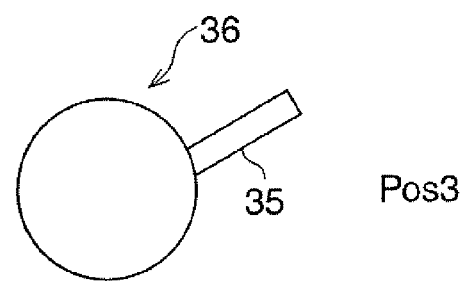

The handle 35 can move further upward from the first position. When the rotation lever 36 is in a position where the handle 35 is in the highest position among its movable positions (hereinafter called the "third position"), the electronic endoscope 10 does not start, because electric power is not supplied to the scope 20 nor to the processor 30. The rotation lever 36 can be moved to the third position in the situation where no scope including the scope 20 is connected to the processor 30. Note that the third position is represented as "Pos 3" in FIG. 4(D) and in FIG. 5, similarly to with the first and the second positions.

As explained above, the scope connection mechanism 32 functions not only as a locking mechanism to keep the scope 20 connected to the processor 30, but also as a power switch for the electronic endoscope 10 by enabling the rotation lever 36 to move to the third position for switching off the power source of the electronic endoscope 10. Note that the third position for switching off the electronic endoscope 10 should not be between the first position and the second position below the first position, so that the third position is located higher than the first position.

When the rotation lever 36 is in the first position "Pos 1", the power source of the secondary circuit 40 is in the on state under the control of the system control circuit 42, and the buffer circuit 50 is in the off state (see FIG. 5). Therefore, when the rotational lever 36 is in the first position "Pos 1", the buffer circuit 50 does not start, and no electric power is supplied to the scope 20, so that a subject can not be observed, although the secondary circuit 40 starts.

When the rotation lever 36 is moved from the first position "Pos 1", to the second position "Pos 2", in the situation where the scope 20 is connected to the processor 30, switch signals are transmitted from the fourth positional switch 46D to the system control circuit 42. Then, under the control of the system control circuit 42 that has received the switch signals, the buffer circuit 50 is also switched on, in addition to the secondary circuit 40, which has been already in the on state. As a result, both the processor 30 and the scope 20 start, so a subject observation becomes possible.

When the rotation lever 36 is moved to the fourth position "Pos 4", between the first position "Pos 1" and the second position "Pos 2", and the system control circuit 42 receives the switch signals from the second positional switches 46B (see FIG. 2), the system control circuit 42 exchanges the on and off state of the buffer circuit 50; that is, the operational state of the buffer circuit 50. Namely, if the rotation lever 36 which is moved from the first position "Pos 1" to the second position "Pos 2" reaches the fourth position "Pos 4", the system control circuit 42 causes the buffer circuit 50 to start, by causing the power source thereof to be in the on state. On the other hand, if the rotation lever 36 which is moved from the second position "Pos 2" to the first position "Pos 1" reaches the fourth position "Pos 4", the system control circuit 42 causes the buffer circuit 50 to stop operating, by causing the power source thereof to be in the off state.

When the rotation lever 36 is moved to the fifth position "Pos 5" between the fourth position "Pos 4" and the second position "Pos 2", the parameters are written in the processor-side memory 48 or the scope-side memory 26, under the control of the system control circuit 42. To control the writing parameters, signals representing that the rotational position of the rotation lever 36 varies are transmitted from the third positional switch 46C to the system control circuit 42.

That is, when the rotation lever 36 that is moved from the fourth position "Pos 4" to the second position "Pos 2" reaches the fifth position "Pos 5", the system control circuit 42 causes the parameter stored in the scope-side memory 26 to be written to the processor-side memory 48. On the other hand, when the rotation lever 36 that is moved from the second position "Pos 2" to the fourth position "Pos 4" reaches the fifth position "Pos 5", the system control circuit 42 causes the parameter used for a subject observation to be written to the scope-side memory 26.

As explained above, parameters stored in the scope-side memory 26 are reliably written to the processor-side memory 48 before a subject observation, and parameters stored in the processor-side memory 48 are reliably written to the scope-side memory 26 when the scope 20 is detached from the processor 30, such as when a subject observation ends. This is achieved by providing the fifth position "Pos 5" for writing parameters in one of the scope-side or processor-side memories 26 or 48, between the fourth position "Pos 4" for switching the operational state of the buffer circuit 50 and the second position "Pos 2" for enabling a subject observation.

In the electronic endoscope 10 of the embodiment, as explained above, parameters suitable for a subject observation are reliably used according to the scope connected to the processor 30. For example, if the scope 20 which has been used for observing a subject is exchanged with the other scope, parameters stored in the scope 20 are reliably prevented from being overwritten by the other parameters stored in a scope-side memory of the newly connected scope, even if the scopes are exchanged during a subject observation. Therefore, it is possible for suitable parameters according to the scope in usage to be reliably written to the processor-side memory 48, and then used.

Further, because the rotation lever 36 can be moved to the third position, in which state the electronic endoscope 10 is not in use, the scope connection mechanism 32 also functions as the power switch of the electronic endoscope 10, so that no other exclusive switch is required, and the structure of the electronic endoscope 10 can thus be simplified.

Note that parameters may be written to the memories only when the system control circuit 42 determines that parameters already written in the scope-side memory 26 or in the processor-side memory 48 are not the same as the parameters newly to be written in.

The rotation lever 36 may move to the third position from the first position as the scope 20 is connected to the processor 30, although it is preferable that the rotation lever 36 can move to the third position from the first position only when the scope 20 is detached from the processor 30, as in this embodiment, reliably to prevent the scope 20 from operating by mistake.

This invention is not limited to that described in the preferred embodiment; namely, various improvements and changes may be made to the present invention without departing from the spirit and scope thereof.

The present disclosure relates to subject matter contained in Japanese Patent Application No. 2006-005974 (filed on Jan. 13, 2006), which is expressly incorporated herein, by reference, in its entirety.

The invention claimed is:

1. An endoscope in which a plurality of scopes are selectively and detachably connected to a processor, said endoscope comprising:
   a scope-side memory provided in each of said scopes, a parameter used for observing a subject being stored in said scope-side memory;
   a connector provided in each of said scopes, said connector being used for connecting said scope to said processor;
   a processor-side memory provided in said processor; and
   a connection member provided in said processor, said connector being connected to said connection member, said connection member being movable between a first position and a second position, said connector being detachably connectable to said connection member when said connection member is in said first position, said subject being observable when said connection member is in said second position, said parameter being written to said processor-side memory when said connection member is moved from said first position to said second position, and said parameter being written to said scope-side memory when said connection member is moved from said second position to said first position.

2. The endoscope according to claim 1, wherein said connection member comprises a rotatable lever.

3. The endoscope according to claim 1, wherein said connection member is movable further to a third position that is not between said first position and said second position, and said processor and said scope do not operate when said connection member is in said third position.

4. The endoscope according to claim 1, wherein said processor further comprises a first electric circuit that can be electrically connected to said scope, said first electric circuit does not operate when said connection member is in said first position, and said first electric circuit operates when said connection member is in said second position.

5. The endoscope according to claim 4, wherein said connection member is movable further to a fourth position where the on and off states of said first electric circuit are switched, and to a fifth position where said parameter is written to said scope-side memory or to said processor-side memory, said fourth position and said fifth position being between said first position and said second position.

6. The endoscope according to claim 5, wherein said fifth position is between said second position and said fourth position.

7. The endoscope according to claim 1, wherein said processor further comprises a second electric circuit in which said processor-side memory is provided, and said second electric circuit operates when said connection member is in said first position or in said second position.

8. The endoscope according to claim 7, wherein said second electric circuit comprises an image processor that processes an image of said subject, said parameter being used for processing said image of said subject.

9. A processor to which one of a plurality of scopes is selectively and detachably connected, each of said scopes comprising a scope-side memory in which a parameter used for observing a subject is stored and a connector that is used for connecting said scope to said processor, said processor comprising:
   a processor-side memory; and
   a connection member to which said connector is connected; said connection member being movable between a first position and a second position, said connector being detachably connectable to said connection member when said connection member is in said first position, said subject being observable when said connection member is in said second position, said parameter being written to said processor-side memory when said connection member is moved from said first position to said second position, and said parameter being written to said scope-side memory when said connection member is moved from said second position to said first position.

10. A scope connection mechanism provided in a processor to which one of a plurality of scopes is selectively and detachably connected, each of said scopes comprising a scope-side memory in which a parameter used for observing a subject is stored, and a connector that is used for connecting said scope to said processor, said processor comprising a processor-side memory, said scope connection mechanism comprising:
    a connection member to which said connector is connected; said connection member being movable between a first position and a second position, said connector being detachably connectable to said connection member when said connection member is in said first position, said subject being observable when said connection member is in said second position, said parameter being written to said processor-side memory when said connection member is moved from said first position to said second position, and said parameter being written to said scope-side memory when said connection member is moved from said second position to said first position.

11. A scope that is selectively and detachably connected to a processor comprising a processor-side memory, said scope comprising:
    a scope-side memory in which a parameter used for observing a subject is stored; said parameter being written to said processor-side memory and said subject being observable when said scope is connected to said processor, said parameter being written to said scope-side memory when scope is detached from said processor, so that said parameter written to said processor-side memory lastly is stored in said scope-side memory.

12. The scope according to claim 11, wherein said parameter is used for processing an image of said subject.

* * * * *